United States Patent
Switzer et al.

(10) Patent No.: US 9,955,343 B2
(45) Date of Patent: Apr. 24, 2018

(54) WIRELESS INITIALIZATION OF ELECTRONIC DEVICES FOR FIRST TIME USE

(71) Applicant: NIKE, Inc., Beaverton, OR (US)

(72) Inventors: David Switzer, Seattle, WA (US); Riyadth Al-Kazily, Seattle, WA (US)

(73) Assignee: NIKE, Inc., Beaverton, OR (US)

(*) Notice: Subject to any disclaimer, the term of this patent is extended or adjusted under 35 U.S.C. 154(b) by 0 days.

(21) Appl. No.: 15/423,732

(22) Filed: Feb. 3, 2017

(65) Prior Publication Data

US 2017/0150346 A1    May 25, 2017

Related U.S. Application Data

(63) Continuation of application No. 14/313,547, filed on Jun. 24, 2014, now Pat. No. 9,612,845.
(Continued)

(51) Int. Cl.
*H04M 3/00*    (2006.01)
*H04W 8/22*    (2009.01)
(Continued)

(52) U.S. Cl.
CPC ............ *H04W 8/22* (2013.01); *A61B 5/0024* (2013.01); *G06F 1/163* (2013.01); *G06F 8/65* (2013.01);
(Continued)

(58) Field of Classification Search
CPC ...... H04W 8/22; A61B 5/0024; A61B 5/6807; A61B 5/7435; A61B 5/0402; A61B 5/11;
(Continued)

(56) References Cited

U.S. PATENT DOCUMENTS 6,882,955 B1    4/2005    Ohlenbusch et al.
7,706,637 B2 *    4/2010    Marriott .................... G06F 8/65
                                              382/276
(Continued)

FOREIGN PATENT DOCUMENTS

EP        2107837 A1    10/2009
JP      2003111152 A    4/2003
(Continued)

OTHER PUBLICATIONS

Oct. 20, 2014—(WO) ISR—App. PCT/US2014/028588.

*Primary Examiner* — Ajit Patel

(74) *Attorney, Agent, or Firm* — Banner & Witcoff, Ltd.

(57) ABSTRACT

Apparatuses, devices, and methods of initializing an electronic device such as a wrist-worn device are provided. An optical input device may read the display of the wrist-worn device to obtain input corresponding to a pairing token presented at the display. An optical input processor may process the input to identify the pairing token. The pairing token may be provided to the wrist-worn device during a handshake process in order to establish a wireless communications session with the wrist-worn device. An initialization process may be performed via the wireless communication session. The initialization process may initialize the wrist-worn device such that a user may operate the wrist-worn device following the initialization process.

16 Claims, 10 Drawing Sheets

Related U.S. Application Data

(60) Provisional application No. 61/841,735, filed on Jul. 1, 2013.

(51) Int. Cl.

| | | |
|---|---|---|
| *G06F 9/44* | (2018.01) | |
| *G06F 9/445* | (2018.01) | |
| *G06F 1/16* | (2006.01) | |
| *A61B 5/00* | (2006.01) | |
| *A61B 5/0402* | (2006.01) | |
| *A61B 5/11* | (2006.01) | |

(52) U.S. Cl.
CPC .......... G06F 9/4401 (2013.01); *A61B 5/0402* (2013.01); *A61B 5/11* (2013.01); *A61B 5/681* (2013.01); *A61B 5/6804* (2013.01); *A61B 5/6807* (2013.01); *A61B 5/7435* (2013.01)

(58) Field of Classification Search
CPC ....... A61B 5/6804; A61B 5/681; G06F 1/163; G06F 9/4401; G06F 8/65
See application file for complete search history.

(56) References Cited

U.S. PATENT DOCUMENTS

| | | | | |
|---|---|---|---|---|
| 8,554,970 | B2 * | 10/2013 | Suumaki | H04W 4/008 370/338 |
| 8,934,839 | B2 * | 1/2015 | Singh | H04W 4/008 340/539.12 |
| 9,585,563 | B2 * | 3/2017 | Mensinger | A61B 5/0004 |
| 2006/0129848 | A1 | 6/2006 | Paksoy et al. | |
| 2008/0016537 | A1 * | 1/2008 | Little | H04L 63/0853 725/81 |
| 2008/0078831 | A1 | 4/2008 | Johnson et al. | |
| 2009/0319673 | A1 * | 12/2009 | Peters | H04W 4/08 709/228 |
| 2010/0115591 | A1 | 5/2010 | Kane-Esrig | |
| 2010/0275010 | A1 | 10/2010 | Ghirardi | |
| 2011/0081860 | A1 | 4/2011 | Brown et al. | |
| 2011/0195780 | A1 * | 8/2011 | Lu | A61B 5/1112 463/31 |
| 2011/0219427 | A1 | 9/2011 | Hito et al. | |
| 2011/0221590 | A1 * | 9/2011 | Baker | A61B 5/0002 340/539.12 |
| 2011/0276304 | A1 * | 11/2011 | Yin | A61B 5/1118 702/141 |
| 2012/0099780 | A1 | 4/2012 | Smith et al. | |
| 2012/0265913 | A1 * | 10/2012 | Suumaki | H04W 4/008 710/303 |
| 2013/0268767 | A1 | 10/2013 | Schrecker | |
| 2013/0278631 | A1 * | 10/2013 | Border | G02B 27/017 345/633 |
| 2013/0325949 | A1 * | 12/2013 | Virani | G06F 9/541 709/204 |
| 2014/0096220 | A1 | 4/2014 | Da Cruz Pinto et al. | |

FOREIGN PATENT DOCUMENTS

| | | |
|---|---|---|
| JP | 2011196760 A | 10/2011 |
| JP | 2012173021 A | 9/2012 |
| WO | 2012021507 A2 | 2/2012 |
| WO | 2013096954 A1 | 6/2013 |

* cited by examiner

WIRELESS INITIALIZATION OF ELECTRONIC DEVICES FOR FIRST TIME USE

CROSS-REFERENCE TO RELATED APPLICATION

This application is a continuation of U.S. patent application Ser. No. 14/313,547 entitled "Wireless Initialization of Electronic Devices for First Time Use" and filed on Jun. 24, 2014, which claims priority to U.S. Provisional Patent Application No. 61/841,735 entitled "Wireless Initialization of Electronic Devices for First Time Use" and filed on Jul. 1, 2013, each of which is incorporated by reference in its entirety herein.

TECHNICAL FIELD

The present disclosure generally relates to initialization of electronic devices and, in particular, relates to wireless initialization of electronic devices for first time use.

BACKGROUND

In order to ensure the best possible performance and user experience, manufacturers may periodically provide updates to the software or firmware of electronic devices. In some situations, a manufacturer may issue a software or firmware update after the electronic device is shipped to a retailer but before a customer purchases the electronic device. As a result, it can be advantageous for a customer to check for any available software or firmware updates before using the electronic device. This process may involve attaching the electronic device to a computing device such as a desktop computer and accessing a remote system to determine whether any software or firmware updates are available.

In other situations, a user may prefer to being using the device as soon as possible after purchase. The user may therefore hope to avoid potentially time-consuming updates. In these situations, however, a minimum amount of configuration settings and preferences may need to be applied before the device is functional for a first-time use. Providing such setting or preferences at the device may also involve attaching the device to a computing device in order to perform an initial configuration of the device.

These initial steps may delay the time between purchase of the device and when the device is ready for use. Having to wait for the device to be functional may diminish the user experience. Therefore, a need exists for improved approaches to initializing electronic devices.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

A computer-implemented method of initializing an electronic device such as a wrist-worn device is provided. An optical input device may read the display of the wrist-worn device to obtain input corresponding to a pairing token presented at the display. An optical input processor may process the input to identify the pairing token. The pairing token may be provided to the wrist-worn device during a handshake process in order to establish a wireless communications session with the wrist-worn device. An initialization process may be performed via the wireless communication session. The initialization process may initialize the wrist-worn device such that a user may operate the wrist-worn device following the initialization process.

The initialization process may be performed before the creation of a user profile for the user and may include a provisioning process and a configuration process. The provisioning process may provide the wrist-worn device firmware updates or software updates. The configuration process may provide the wrist-worn device with configuration information and user profile information.

A wrist-worn device that obtains information corresponding to movements of a user while the user wears the device is also provided. The wrist-worn device may include a pairing token generator that generates a pairing token locally at the wrist-worn device. The wrist-worn device may present the paring token at a display. A configuration device may thus optically read the pairing token presented at the display. The wrist-worn device and the configuration device may use the pairing token to establish a wireless communications session and automatically initiate an initialization process once the wireless communication is established. The pairing token generator may automatically generate the pairing token in response to an initial activation of the device. The pairing token generator may also generate the pairing token in response to user input received at the wrist-worn device.

An apparatus for initializing a wrist-worn device is further provided. An optical input device may obtain input from the wrist-worn device. The input may correspond to a pairing token presented at a display of the device. An optical input processor may process the input to identify the pairing token. A configuration application may provide the pairing token to the wrist-worn device during a handshake process in order to establish a wireless communication session with the wrist-worn device. The configuration application may also perform an initialization process via the wireless communication session that initializes the wrist-worn device. Following the initialization process, the wrist-worn device may be available for operation by a user.

The pairing token may be a string of numeric, alphabetic, or alphanumeric characters, a barcode, an image, a pattern, or a solid color. Accordingly, the optical input processor may be an optical character recognition module, a barcode reader, an image processing module, a pattern recognition module, or a color recognition module. The pairing token may also be a scrolling pairing token that scrolls across the display of the wrist-worn device or a flashing pairing token that flashes at the wrist-worn device when presented. These and other aspects will be discussed in further detail below.

BRIEF DESCRIPTION OF THE DRAWINGS

The present disclosure is illustrated by way of example and not limited in the accompanying figures in which like reference numerals indicate similar elements and in which.

DETAILED DESCRIPTION

Aspects of this disclosure are directed towards wireless initialization of electronic devices. In particular, the principles provided in this disclosure may be employed to wirelessly initialize an electronic device for first time use. It will be appreciated with the benefit of this disclosure, however, that the principles provided may also be employed to wirelessly configure an electronic device subsequent to an initial use of the device. The approaches described in further detail below may be employed to initialize various types of wireless devices. By way of example, the description set forth below proceeds in the context of a wrist-worn sensor assembly device ("wrist-worn device") that obtains information corresponding to the movements of a user while wearing the device. It will also be appreciated, however, that the principles described below may be employed in additional or alternative contexts for additional or alternative types of electronic devices.

As used in this description, initialization of an electronic device refers to adding, removing, or modifying data at the electronic device to provision and configure the electronic device. Initializing the electronic device may include, for example, providing the electronic device with the most up-to-date software or firmware, setting or modifying operational settings or preferences, setting or modifying profile information associated with a user of the electronic device, and other types of configuration or modification of information or data residing at the device. Setting and modifying operational settings, preferences, profile information, and other information or data at the electronic device may also be referred to as configuring the electronic device.

In the following description, reference is made to the accompanying drawings that illustrate various example embodiments in which aspects of the disclosure may be practiced. It is to be understood that other embodiments may be utilized and various structural and functional modifications may be made without departing from the scope and spirit of the present disclosure. Additionally, the various methods provided in this disclosure should not be construed as limited to the particular sequence disclosed. Additional and alternative orderings of various steps may be selectively employed. Furthermore, headings within this disclosure should not be considered as limiting aspects of the disclosure, and the example embodiments are not limited to the example headings.

1. Example Personal Training System

1.1 Illustrative Networks

Figure 1:
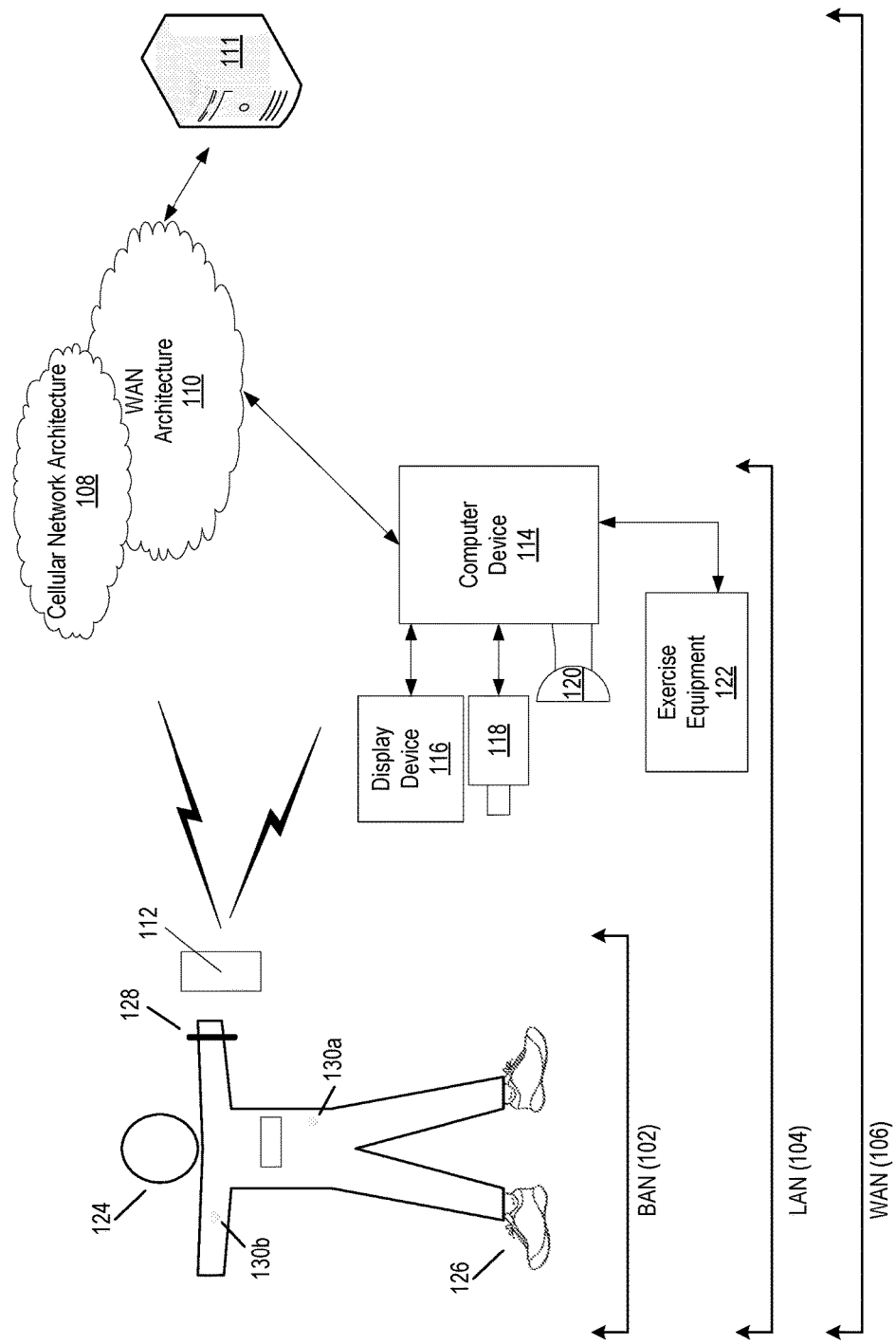
FIG. 1 illustrates an example system that may be configured to provide personal training and/or obtain data from the physical movements of a user.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1.1.1 Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Figure 2:
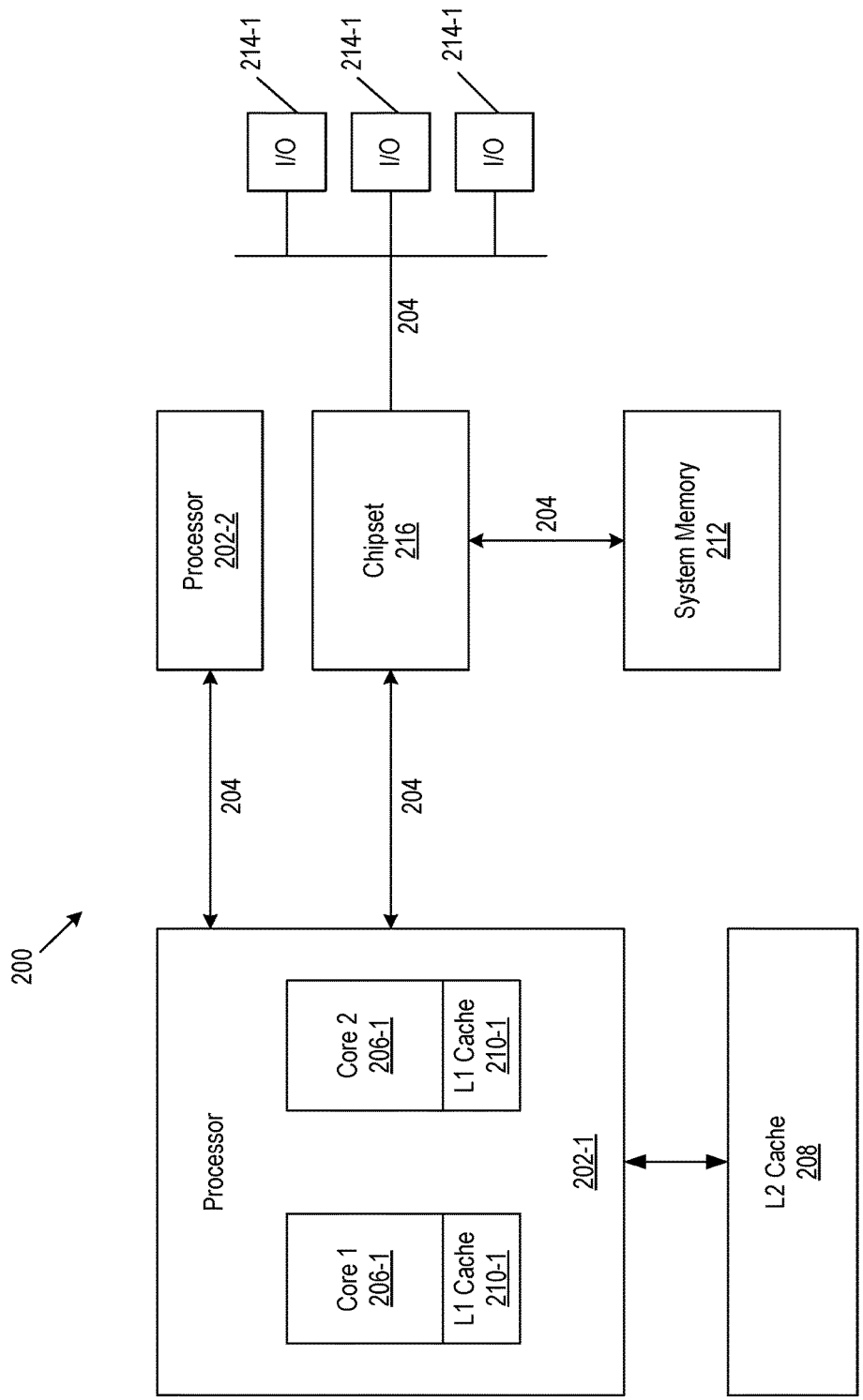
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise sever 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

1.1.2 Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access points permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such one or more of the sensors discussed above in relation to FIGS. 1-3, that may provide information utilized, either independently or in conjunction with other sensors, such as one or more sensors associated with one or more structures. For example, a backboard may comprise a first sensors configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

1.1.2.1 Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an-all day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

1.1.2.1.1 Shoe-Mounted Device

Figure 3:
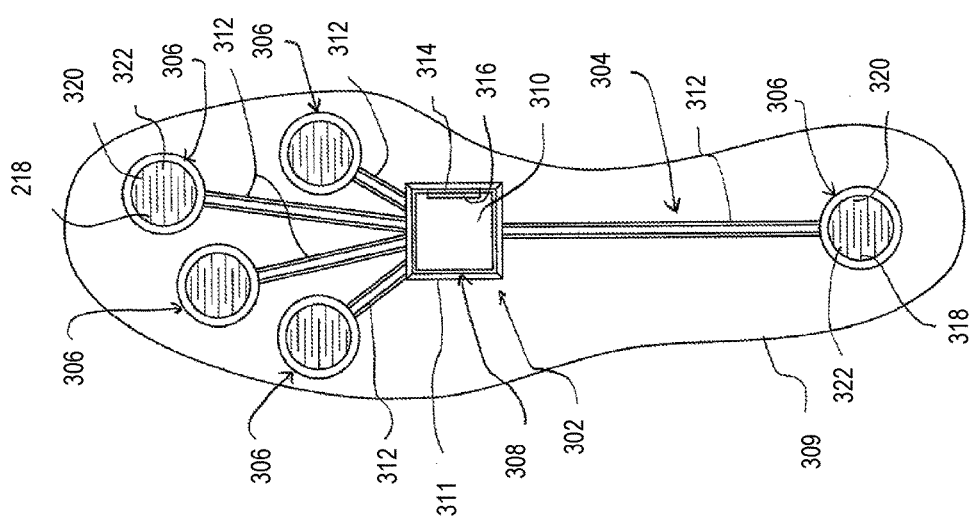
FIG. 3 shows an example of an implementation of a sensor assembly that may be worn by a user.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance" may be measured, which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

1.1.2.1.2 Wrist-Worn Device

Figure 4:
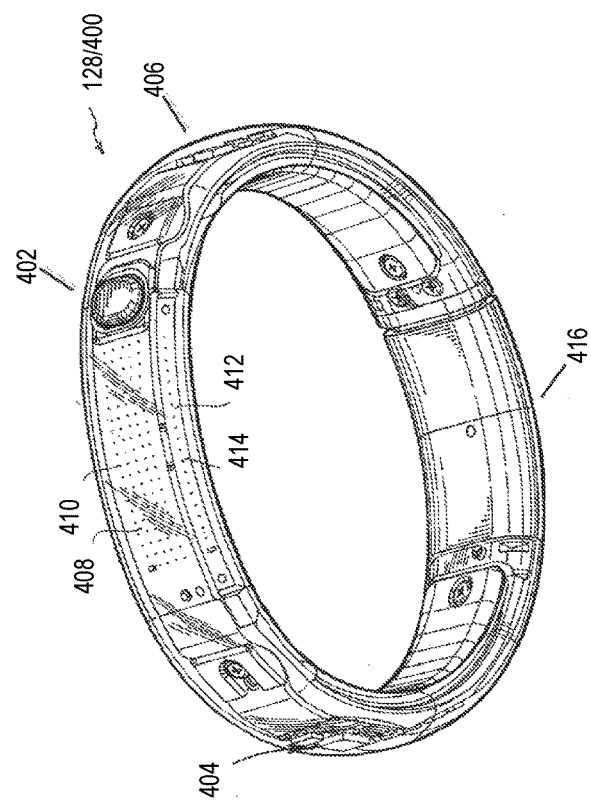
FIG. 4 shows another example of an implementation of a sensor assembly that may be worn by a user.

As shown in FIG. 4, device 400 (which may resemble or comprise sensory device 128 shown in FIG. 1, may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

1.1.2.1.3 Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130*a* and 130*b* may be sensors integrated into apparel, such as athletic clothing. Such sensors may be placed at any desired location of the body of user 124. Sensors 130*a/b* may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
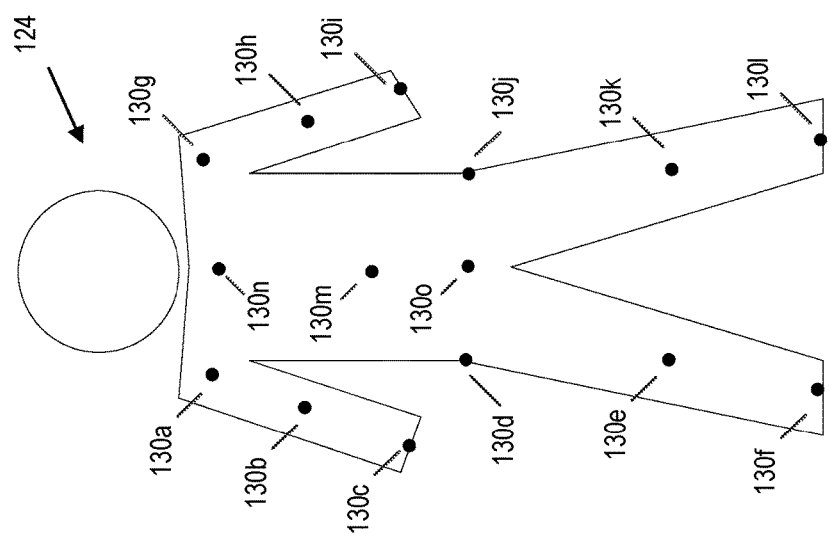
FIG. 5 shows illustrative locations for sensory input that may include physical sensors located on or in the clothing of a user and/or be based upon identification of relationships between two moving body parts of the user.

FIG. 5 shows illustrative locations for sensory input (see, e.g., sensory locations 130*a*-130*o*). In this regard, sensors may be physical sensors located on/in a user's clothing, yet in other embodiments, sensor locations 130*a*-130*o* may be based upon identification of relationships between two moving body parts. For example, sensor location 130*a* may be determined by identifying motions of user 124 with an image-capturing device, such as image-capturing device 118. Thus, in certain embodiments, a sensor may not physically be located at a specific location (such as one or more of sensor locations 130*a*-130*o*), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130*m* may be utilized in a determination of the user's center of gravity (a.k.a, center of mass). For example, relationships between location 130*a* and location(s) 130*f*/130*l* with respect to one or more of location(s) 130*m*-130*o* may be utilized to determine if a user's center of gravity has been elevated along the vertical axis (such as during a jump) or if a user is attempting to "fake" a jump by bending and flexing their knees. In one embodiment, sensor location 1306*n* may be located at about the sternum of user 124. Likewise, sensor location 130*o* may be located approximate to the naval of user 124. In certain embodiments, data from sensor locations 130*m*-130*o* may be utilized (alone or in combination with other data) to determine the center of gravity for user 124.

In further embodiments, relationships between multiple several sensor locations, such as sensors 130*m*-130*o*, may be utilized in determining orientation of the user 124 and/or rotational forces, such as twisting of user's 124 torso. Further, one or more locations, such as location(s), may be utilized to as a center of moment location. For example, in one embodiment, one or more of location(s) 130*m*-130*o* may serve as a point for a center of moment location of user 124. In another embodiment, one or more locations may serve as a center of moment of specific body parts or regions.

2. Wireless Initialization of Electronic Devices

Figure 6:
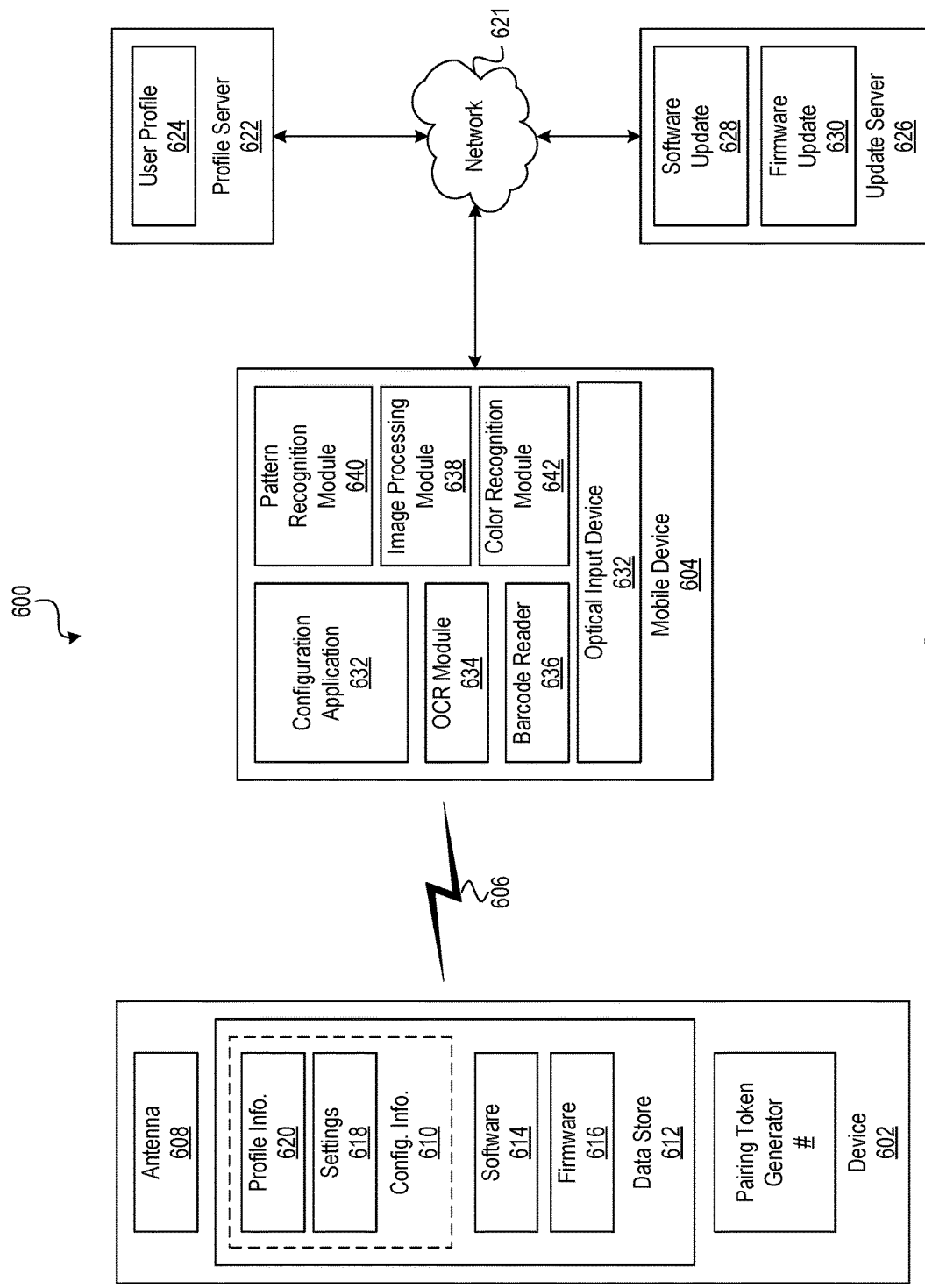
FIG. 6 is an example of an implementation of a system for wirelessly initializing an electronic device.

As indicated above, aspects of this disclosure are directed towards wireless initialization of an electronic device, e.g., for first time use of the electronic device. In FIG. 6, an example of an implementation of a system 600 for wirelessly initializing an electronic device 602 is shown. The electronic device 602 may establish a wireless communication session with a computing device such as a mobile device 604 as shown by way of example in FIG. 6. The mobile device 604 may be, e.g., a mobile telephone, a palmtop computer, a personal digital assistant, a tablet computer, a laptop computer, and other types portable computing devices configured for wireless communication. The electronic device 602 and the mobile device 604 may exchange wireless communications 606 in order to establish the communication session and exchange wireless communications once the communication sessions has been established. Through the communication session, the mobile device 604 may initialize and configure the electronic device, e.g., for first time use. In this regard, the computing device 604 may also be referred to as a configuration device.

The electronic device 602 may include various components that facilitate wireless communications including, e.g., an antenna 608, a radio module (not shown), and other components that facilitate wireless communication. Bluetooth is one example of a wireless technology standard that may be employed to communicate between the electronic device 602 and the mobile computing device 604. Additionally or alternatively other wireless technology standards that may be selectively employed include, e.g., Wireless USB, ZigBee, and other wireless technology standards suitable for establishing, maintaining, and utilizing a communication session between the electronic device 602 and the computing device 604.

As the mobile device 604 may be employed to initialize the electronic device 602, the electronic device may store configuration information 610 at one or more data stores 612. The data stores 612 of the electronic device 602 may include one or more volatile memory devices, one or more non-volatile memory devices, and combinations of such. The data store 612 may store the configuration information 610 as well as software 614 that runs at the electronic device. The data stores 612 may also include hardware components at which firmware 616 resides to control operation of the hardware components. Although only one data store 612 is shown by way of example in FIG. 6, the electronic device 602 may include multiple data stores 612 across which the configuration information 610, software 612, and firmware is distributed.

Configuration information may include, for example, configuration settings 618 as well as profile information 620. Configuration settings may include, for example, preferences that allow a user to customize operation of the device 602. As indicated above, the electronic device 602 may be, in some example implementations, a wrist-worn device that monitors movements of the user and calculates energy expenditure points based on those movements. The wrist-worn device may calculate the energy expenditure points based on, e.g., the physical characteristics of the user. The wrist-worn device may thus account for the particular height, weight, and gender of the user when calculating the energy expenditure points. Accordingly, user profile information 620, in this example, may include, e.g., the height, weight, and gender of the user. It will be appreciated that the configuration information 610 may include other types of information related to the operation or use of the electronic device 602.

The computing device 604 may be in signal communication with other systems via a network 621, e.g., the Internet, As an example, the computing device 604 may be in signal communication with a profile server 622 that maintains a user profile 624 for the user of the electronic device 602. Where the electronic device 602 is a wrist-worn device the user profile 624 may track the energy expenditure points calculated by the device. The device 602 may upload the energy expenditure points to the profile server 622 via the mobile device 604, and the profile server may store the uploaded energy expenditure points and associate the points with the user profile 624 corresponding to the user of the wrist-worn device.

The computing device 604 may also be in signal communication with an update server 626 via the network 621. The update server 626 may store software updates 628 and firmware updates 630 for the electronic device 602. The mobile device 604 may access the update server 626 on behalf of the electronic device 602 to obtain the software updates 628 and firmware updates 630. The mobile device 604 may download the software updates 628 and firmware updates 630 and propagate the updates to the electronic device 602 for installation.

The mobile device 604 may include a configuration application 632 to facilitate communications at the mobile device. The configuration application 632 may, for example, initiate, establish, and maintain the wireless communication session with the electronic device 602. In some example implementations, the configuration application 632 may facilitate transfer of profile information 620 between the electronic device 602, the mobile device 604, and the profile server 622. A user may also utilize the configuration application 632 to view, set, and modify configuration settings 618 at the electronic device 602. Additionally, the configuration application 632 may obtain information relating to the status of software 614 and firmware 616 at the electronic device 602 and query the update server 626 to determine whether the software and firmware are up-to-date. If the software 614 or firmware 616 is not up-to-date, the configuration application 632 may request appropriate software updates 628 or firmware updates 630 from the update server 626. The configuration application 632 may transfer the software updates 628 or firmware updates 630 to the electronic device 602 for installation.

The electronic device 602 and the mobile device 604 establish a wireless communication session to enable these example wireless communications 606. In order to establish the communication session, the electronic device 602 may make itself discoverable, and the mobile device 604 may search for discoverable devices. The configuration application 632 may initiate the discovery process, e.g., in response to user input at the mobile device. As an example, a user may select a button at the configuration application 632 to initiate the device discovery process. In some example implementations, the mobile device 604 and the configuration application 632 may be configured to listen for signals from any devices announcing their presence. Upon discovering the electronic device 602, the configuration application 632 may initiate a handshake process to pair the mobile device 604 with the electronic device 602. After a successful handshake the electronic device 602 and mobile device 604 may be paired and exchange wireless communications 606, e.g., via Bluetooth.

The electronic device 602 and the mobile device 604 may employ a pairing token to pair with each other. In one example implementation, the electronic device 602 itself may generate the pairing token and present it to the mobile device 604. Stated differently, the pairing token may be locally generated by the electronic device 602 and presented to the mobile device 604. The electronic device 602 may dynamically and randomly generate the pairing token. Accordingly, the parsing token may be different for each executed pairing process. In turn, the mobile device 604 may read the pairing token from the electronic device 602 and use the pairing token during the handshake process used to establish the wireless communication session with the electronic device. The electronic device 602 may present the pairing token at its display (e.g., display 408 in FIG. 4) for optical reading and recognition by the mobile device 604. In this regard, the system 600 allows for an optical pairing process between the electronic device 602 and the mobile device 604. The optical pairing process may also be referred to as an optical association process. As used in this disclosure, an optical pairing process refers to a pairing process that involves the use of visible light or invisible light (e.g., infrared light) to communicate the pairing token.

Various types of pairing tokens may be selectively employed. As noted above, the pairing tokens may be optical pairing tokens for an optical pairing process. Examples of pairing tokens include a string of numeric characters (e.g., a personal identification number—PIN), a string of alphabetic characters (e.g., a code word), and a string of alphanumeric characters. Other examples of pairing tokens may include linear barcodes and two-dimensional (2D) barcodes (e.g., a QR Code, a DotCode, and other types of matrix barcodes). In some example implementations, the pairing token may be a set of one or more images or a pattern presented at the display of the electronic device 602. The pattern may be a single color or multicolor. An image may be, e.g., a symbol, an ideogram, a pictogram, and other types of graphics. The pairing token may also be a solid color, e.g., a colored or pigmented pairing token. In some example implementations, the electronic device may be configured to scroll the pairing toking across its display, e.g., a scrolling alphanumeric pairing token. In other example embodiments, the electronic device may also be configured to present the pairing token by flashing the display, e.g., a flashing pairing token. A mobile device, in this case, may record the flashes to identify the pairing token based on, e.g., the number of flashes, the duration of the flashes, and combinations of such. The flashes may also be flashes of one or multiple colors. FIGS. 9-17 illustrate example pairing tokens that may be selectively employed.

The mobile device 604 may include various input and processing components to read and identify the pairing token presented at the display of the electronic device. In this regard, the mobile device 604 may obtain input via these components and process the input to identify the pairing token generated and presented by the electronic device 602. As shown by way of example in FIG. 6, the mobile device 604 includes an optical input device 632 to capture optical input of the display containing the pairing token. The optical input device 632 may be, e.g., a camera, barcode scanner, image scanner, and other types of optical input devices. The mobile device may include one or more optical input processing modules to process the optical input and identify the pairing token. The optical input processing module may also be referred to as an optical input processor or optical input processing device.

Where the pairing token is a string of numeric, alphabetic, or alphanumeric characters, the optical input processing module may be an optical character recognition (OCR) module 634 to process the input image and recognize the pairing token contained in the input image. Having recognized the pairing token from the input image, the OCR module 634 may provide the pairing token to the configuration application 632 for use during the handshake process with the electronic device 602. The OCR module 634 may also be referred to as an optical character recognizer or an OCR device. The pairing token in the input image may also be, e.g., a barcode, an image, a pattern, or a solid color as noted above. Accordingly, the optical input processing module may be, e.g., a barcode reading module 636, an image processing module 638, a pattern recognition module 640, or a color recognition module 642. The barcode reading module 636 may also be referred to as a barcode reader or a barcode reading device; the image processing module 638 may also be referred to as an image processor or image processing device; the pattern recognition module 640 may also be referred to as a pattern recognizer or pattern recognition device; and the color recognition module 642 may also be referred to as a color recognizer or a color recognition device. The mobile device 604 may include one, some, or all of these example optical input processing modules 634-640, and these example modules may be part of the configuration application 632 or separate modules in signal communication with the configuration application.

The barcode reading module 636 may be configured to recognize one or more types of barcodes contained in the input image, e.g., linear barcodes or 2D barcodes. The image processing module 638 may be configured to identify the image generated by the electronic device 602 and presented at its display. In some example implementations, a set of images may be respectively associated with a PIN. Having identified the image, the image processing module 638 may perform a lookup to determine the particular PIN associated with the identified image. The image processing module 638 may then provide the configuration application 632 with the PIN for use during the handshake process with the electronic device 602. The pattern recognition module 640 may identify the pairing token in a similar fashion. The pattern recognition module 640 may be configured to identify the pattern generated by the electronic device 602 and presented at its display. A set of one or more patterns may also be respectively associated with a PIN. Having identified the pattern, the pattern recognition module 640 may perform a lookup to determine the particular PIN associated with the identified pattern and provide the PIN to the configuration application 632 for use during the handshake process. This example lookup process may also be employed where the pairing token is a solid color. A set of one or more colors may be respectively associated with a PIN, and a color recognition module 642 may perform a lookup to determine the particular PIN associated with an identified color.

Figure 7:
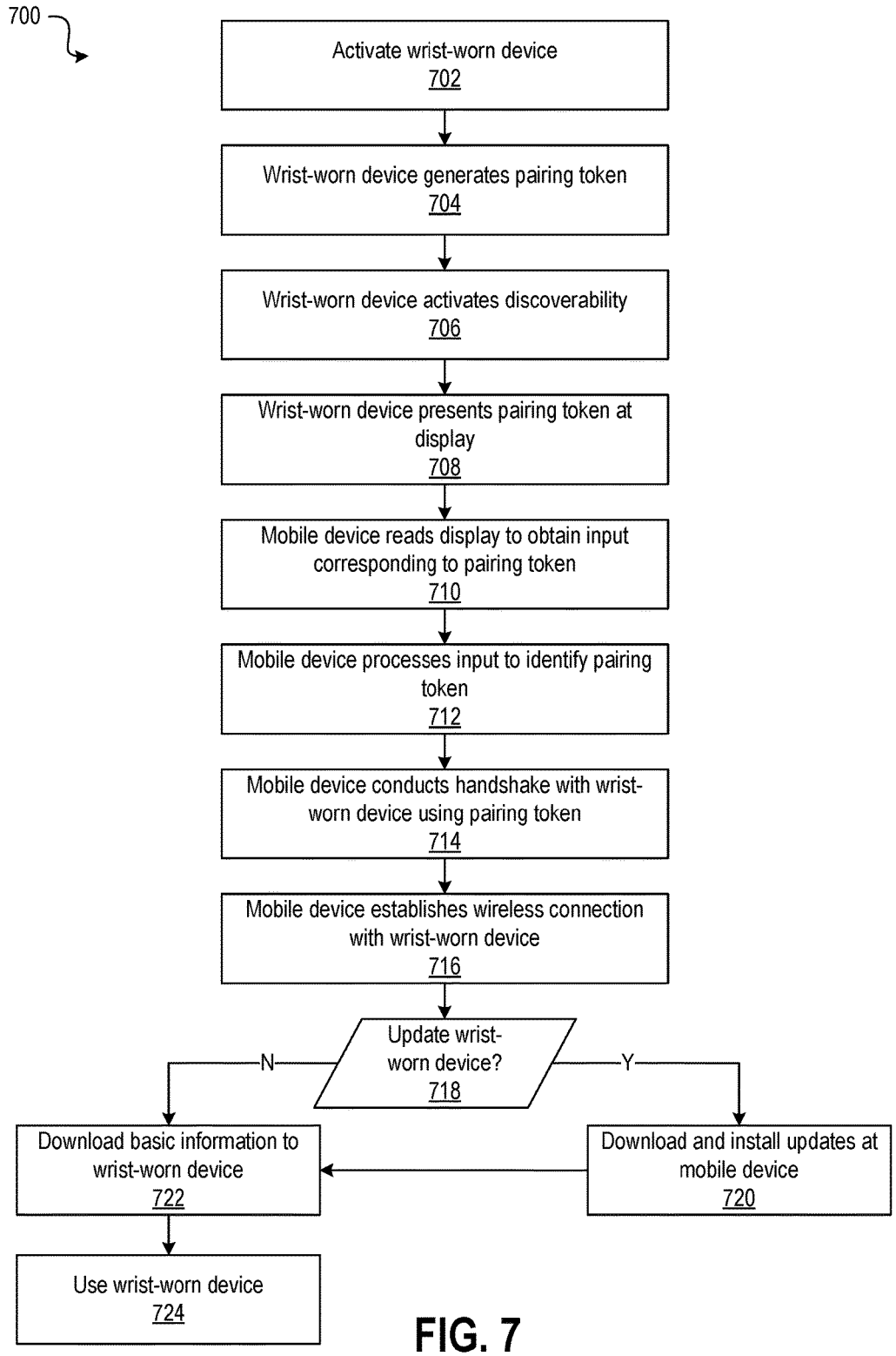
FIG. 7 is a flowchart of example method steps for wirelessly initializing an electronic device.

In FIG. 7, a flowchart 700 of example method steps for wirelessly initializing an electronic device is shown. The methods steps, in this example, may be performed to initialize the electronic device for first time use or to subsequently configure the electronic device after a first time use. A user may first activate the electronic device (block 702). As noted above, the electronic device may be a wrist-worn device that monitors the movements of the user and calculates energy expenditure points. Once activated, the wrist-worn device may generate a pairing token (block 704) to use when establishing a wireless connection with another computing device. As discussed above, the computing device may be a mobile device thereby allowing a user to initialize the wrist-worn device remotely. The electronic device may be configured to generate the pairing token automatically or in response to receipt of user input. For example, the wrist-worn device may be configured to identify an initial activation of the device and automatically generate a pairing token in response. In another example, the wrist-worn device may generate the pairing token in response to user activation of an input button at the device.

The wrist-worn device may then make itself discoverable (block 706) to nearby computing devices. The wrist-worn device may be similarly configured to activate discoverability automatically or in response to receipt of user input. The wrist-worn device may present the pairing token at its display (block 708) for reading by the mobile device. As noted above, the pairing process may be an optical associated process. Accordingly, the mobile device may read the display of the wrist-worn device to obtain input corresponding to the pairing token (block 710). The mobile device may process the input to identify or recognize the pairing token (block 712). As described above, the mobile device may include a configuration application or one or more modules to process the input. As the pairing token may be a string of characters, an image, a barcode, a pattern, and so forth, the modules may respectively include one or more of an OCR module, image recognition module, barcode reading module, pattern recognition module, and color recognition module.

Having recognized the pairing token, the mobile device may initiate a handshake process with the wrist-worn device using the recognized pairing token (block 714). If the pairing token provided by the mobile device matches the pairing token generated by the wrist-worn device, then the devices may establish a communication session for exchanging wireless communications (block 716). Once the communication is established, various initialization processes may be automatically initiated to initialize the wrist-worn device. The initialization processes may be initiated by the configuration application or the wrist-worn device itself, e.g., by transmitting a command signal to the configuration application that instructs the configuration application to perform the initialization process. One example initialization process may be a provisioning process in which the configuration application determines whether the software or firmware at the wrist-worn device is up-to-date and provides the most up-to-date software if not. If the configuration application determines that the wrist-worn device does not include the most recent software or firmware (block 718:Y), then the mobile device may download and install software or firmware updates at the wrist-worn device (block 720). If the configuration application determines that the software or firmware at the wrist-worn device does not need to be update (block 718:N), then the configuration application may download information to the wrist-worn device (block 722), such as, e.g., configuration settings, profile information and other information and data. It will be appreciated that the configuration application may also retrieve information from the wrist-worn device, e.g., profile information for uploading to a profile server as described above. With the wrist-worn device updated and configured, the wrist-worn device is ready for use (block 724).

Figure 8:
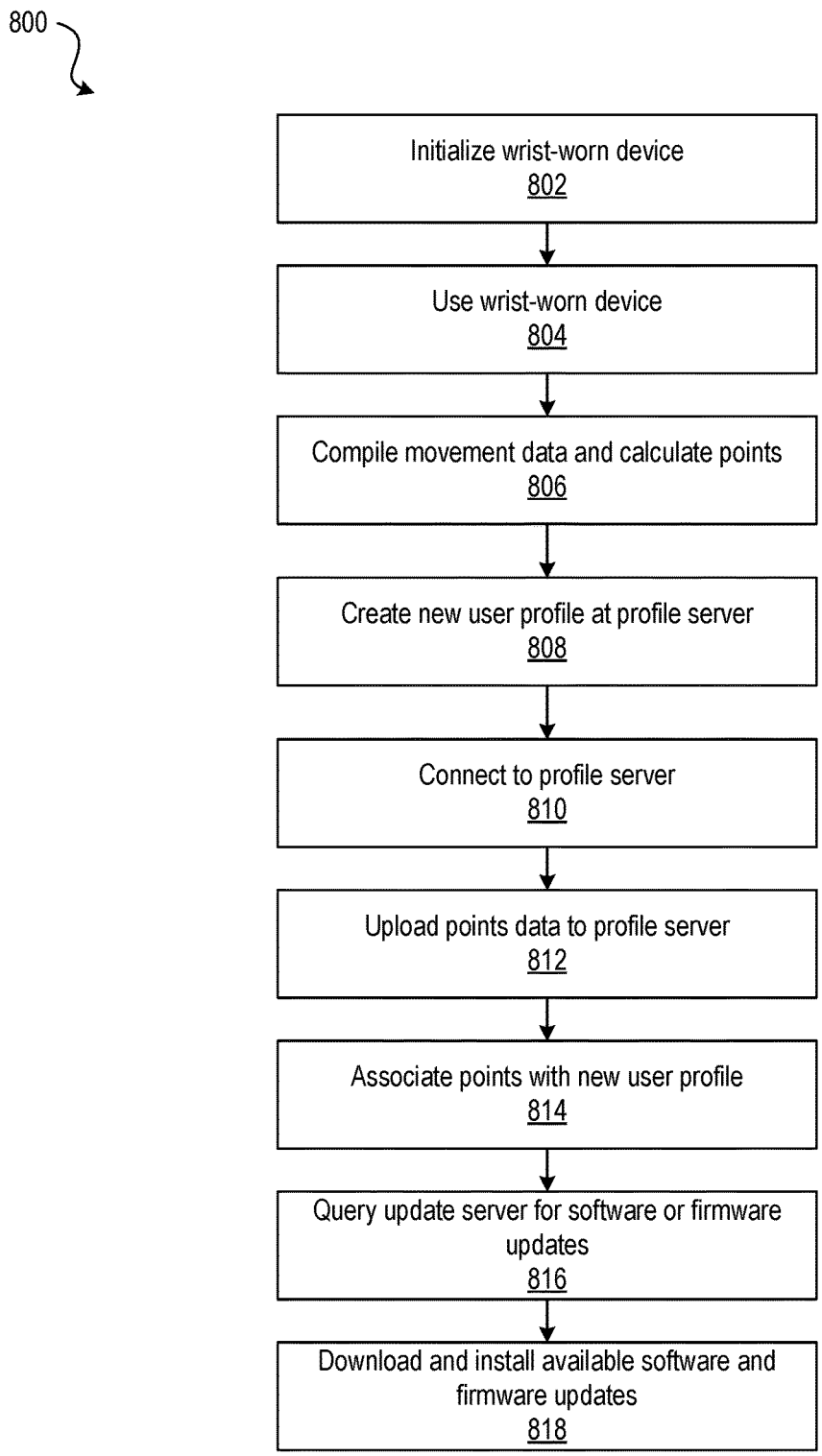
FIG. 8 is another flowchart of example method steps for wirelessly initializing an electronic device.

Another example of an initialization process is a configuration process in which the configuration application downloads configuration information or profile information to the wrist-worn device. In FIG. 8, another flowchart 800 of example method steps for wirelessly initializing a wrist-worn device that monitors and collects information corresponding to the movements of a user wearing the device is shown. The steps, in this example, illustrate that a user may initialize the wrist-worn device (block 802) and begin using the device (block 804) before creating a profile with which to associate the collected data and before updating the software or firmware at the device. As described above, the user may remotely initialize a wrist-worn device for first time use via a mobile device thereby allowing the user to begin using the device almost immediately after purchase and defer creation of a user account and associated user profile until after first use of the device. The user may also defer downloading and installing any software or firmware updates until after the first use of the device.

Through the remote configuration process, the user may provide the wrist-worn device, in this example, with the minimum information needed to calculate energy expenditure points, e.g., gender, height, and weight. With the wrist-worn device configured and ready for use, a user may almost immediately begin compiling movement data and calculating energy expenditure points (block 806). Subsequent to the first time use of the wrist-worn device, the user may then create a user profile, e.g., at a user profile server (block 808), connect to the profile server (block 810), and upload the calculated energy expenditure points (block 812) for association with the newly created user profile (block 814). The user may connect to the user profile and upload the energy expenditure points via the configuration application at the mobile device or a configuration application at a desktop computing device. After the first use of the wrist-worn device, the user may query the update server via a computing device to determine whether any software or firmware updates are available (block 816) and download and install any available software or firmware updates if so (block 818).

As seen in this example, a user may begin utilizing the wrist-worn device as soon as it is initialized. Through the approaches described above, the user may remotely initialize and begin using the device almost immediately after purchase. The user may thus defer creation of a user account and profile as well as any software or firmware updates until such a time that it is convenient for the user. An example scenario may be as follows. A user may purchase the wrist-worn device from a retailer. Using a mobile phone, the user may initialize the wrist-worn device to provide the basic profile information (e.g., height, weight, and gender) used to calculate the energy expenditure points. Once configured, the user may attach the wrist-worn device and start collecting initial movement data and calculate initial energy expenditure points throughout the remainder of the day. Once the user returns home, the user may log on to the profile server (e.g., at a desktop computer), create a new account, and provide more detailed profile information for the user profile for the new user account. The user may then upload the initial movement data and initial energy expenditure points previously obtained following the purchase of the device. The user may then attach the wrist-worn device to a charging station overnight and leave the device activated. While the device is charging, the device may automatically establish a wireless communication session with a configuration application at a computing device to download and install any available software or firmware updates. In this way, the delay between when a user purchases the device and when the user can first use the device is advantageously minimized and a more enjoyable user experience is achieved.

As noted above, the example approaches described may be employed to keep the wrist-worn device up to date as new software updates and firmware updates become available. As an example, a user may recharge the wrist-worn device by attaching it to a charging station, e.g., a USB charging station. Instead of deactivating the radio of the device, the wrist-worn device may keep the radio active in order to establish and maintain a wireless communication session with the mobile device. The configuration application at the mobile device may periodically query the update server to determine whether any new software updates or firmware updates are available. If a new software update or firmware update is available, then the configuration application may automatically initiate a provisioning process to provide the new software update or firmware update to the wrist-worn device. In this way, the wrist-worn device may be automatically updated with the latest software and firmware while the wrist-worn device is not in use, e.g., while the wrist worn device is charging.

Figure 9:
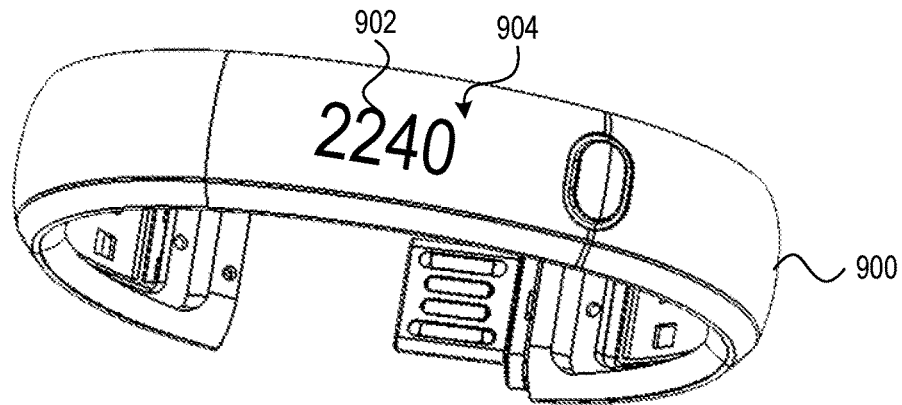
FIG. 9 is an example of a first type of pairing token.
Figure 10:
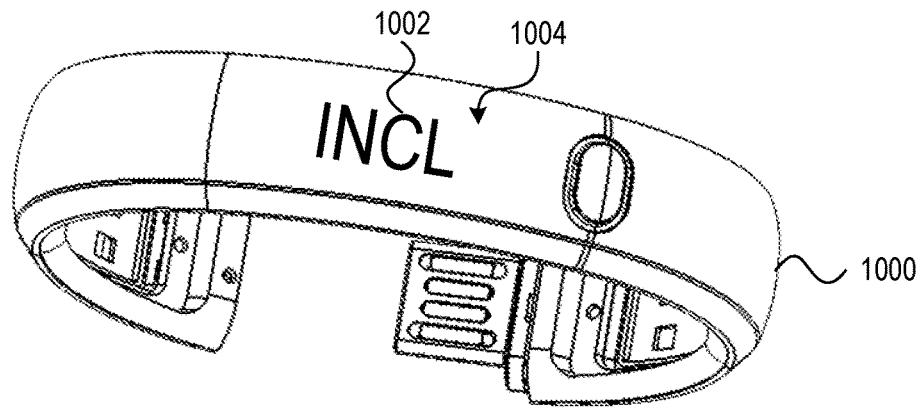
FIG. 10 is an example of a second type of pairing token.
Figure 11:
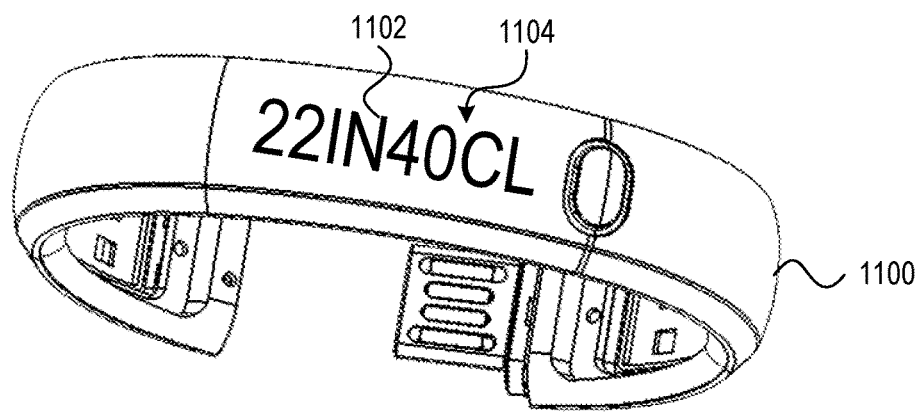
FIG. 11 is an example of a third type of pairing token.

FIGS. 9-17 illustrate example pairing tokens that may be selectively employed when performing wireless initialization of an electronic device. As seen in these figures, the electronic device, in this example, is a wrist-worn device for monitoring and collecting information corresponding to the movements of a user wearing the device. As noted above, the pairing token may be a numeric, alphabetic, or alphanumeric string. In FIG. 9, the device 900 presents an example of a numeric pairing token 902 at its display 904. In FIG. 10, the device 1000 presents an example of an alphabetic pairing token 1002 at its display 1004. In FIG. 11, the device 1100 presents an example of an alphanumeric pairing token 1102 at its display 1104.

Figure 12:
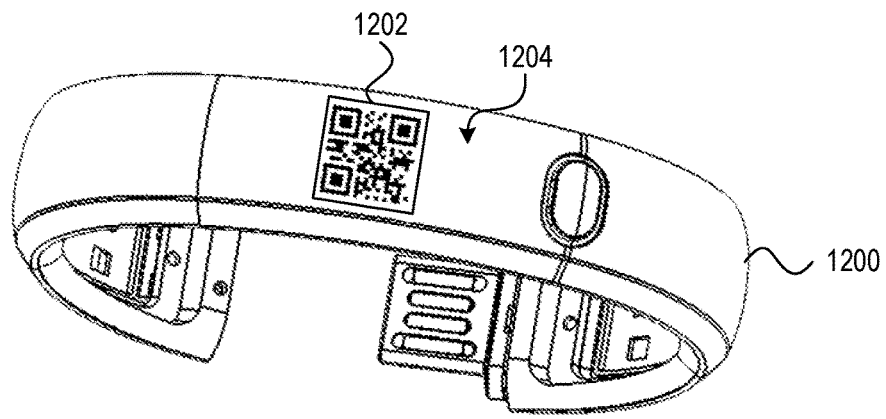
FIG. 12 is an example of a fourth type of pairing token.
Figure 13:
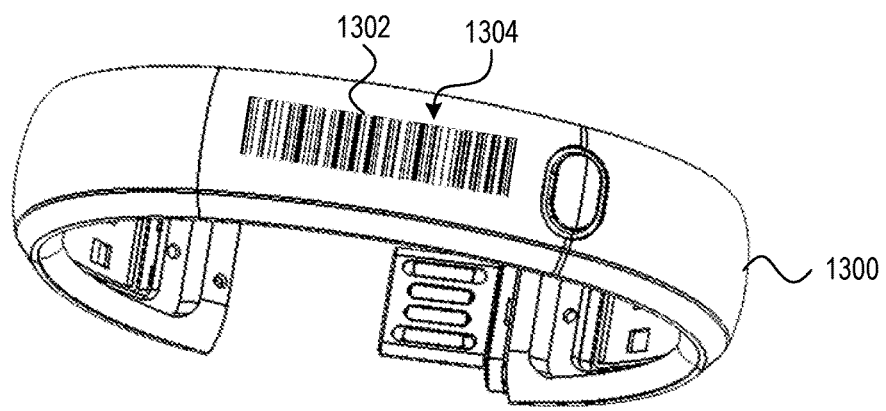
FIG. 13 is an example of a fifth type of pairing token.
Figure 14:
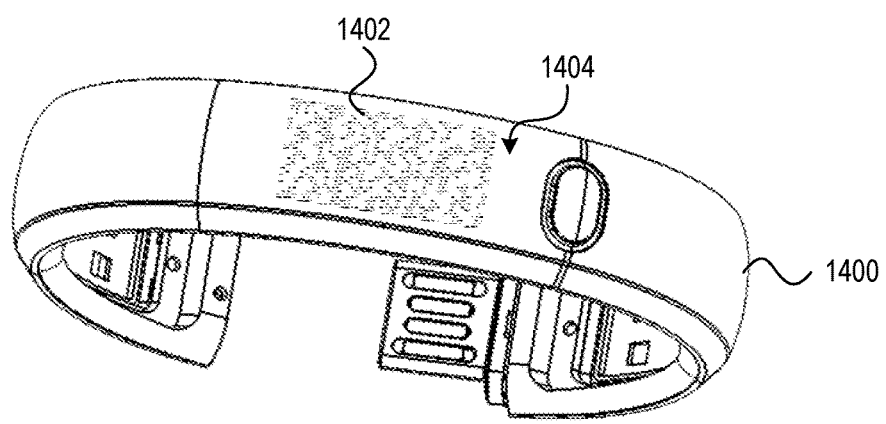
FIG. 14 is an example of a sixth type of pairing token.
Figure 15:
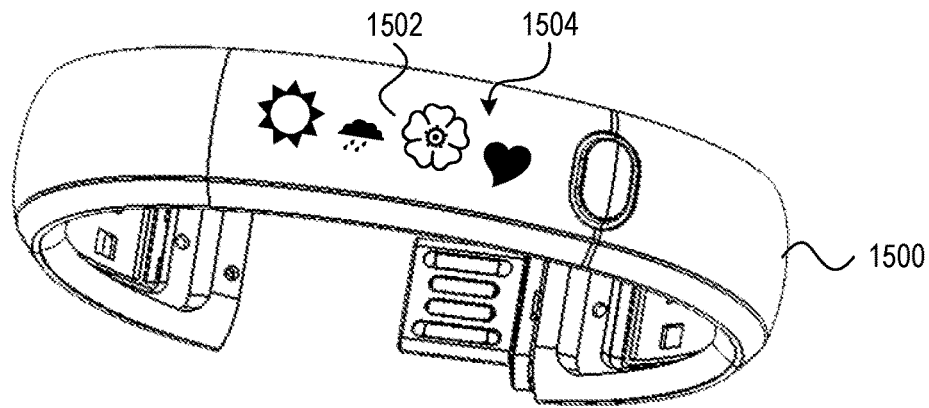
FIG. 15 is an example of a seventh type of pairing token.
Figure 16:
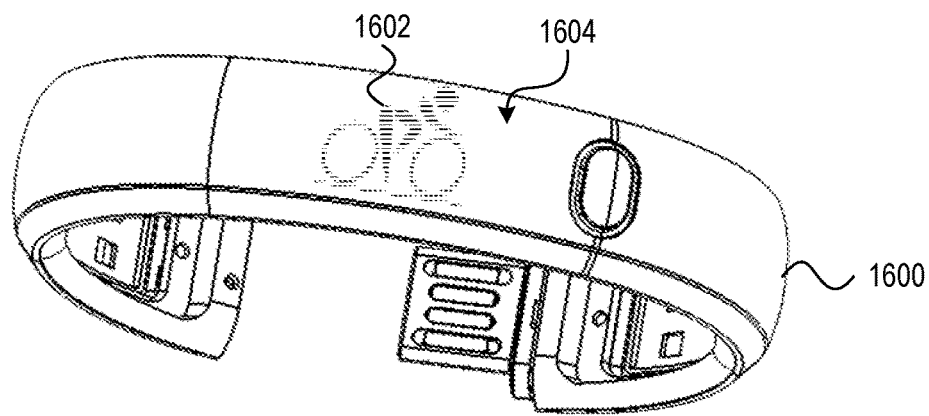
FIG. 16 is an example of an eighth type of pairing token.
Figure 17:
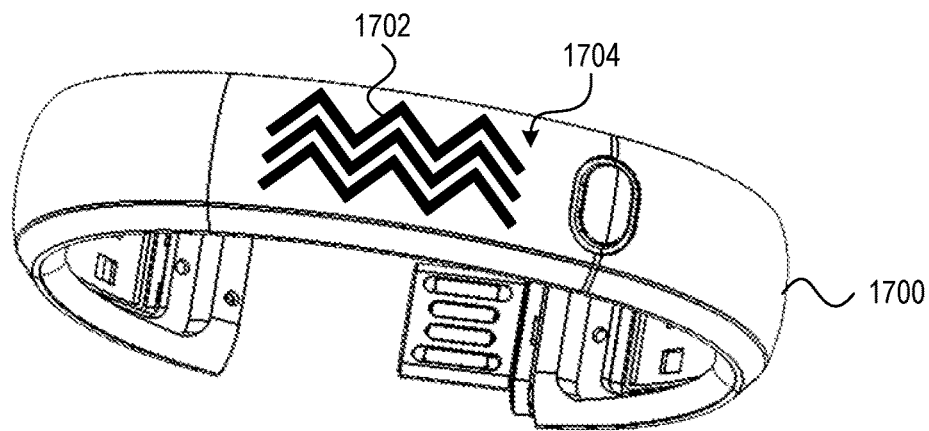
FIG. 17 is an example of a ninth type of pairing token.

As also noted above, the pairing token may be a linear or 2D barcode. In FIG. 12, the device 1200 presents a pairing token 1202 at the display 1204 as a 2D barcode, e.g., a QR code matrix. In FIG. 13, the device 1300 presents a pairing token 1302 at the display 1304 as a linear barcode, e.g., a Code 128 barcode. In FIG. 14, the device 1400 present a pairing token 1402 at the display 1404 as another type of 2D barcode, e.g., a DotCode matrix. Moreover, the pairing token may be a set of one or more images or a pattern as also described above. In FIG. 15, the device 1500 presents a pairing token 1502 at the display 1504 as a set of four symbols. In FIG. 16, the device 1600 presents a pairing token 1602 at the display 1604 as an image. In FIG. 17, the device 1700 presents a pairing token 1702 at the display 1704 as a pattern.

The mobile device used to pair with the electronic device may be configured to capture these pairing tokens as input and then process the input to determine the pairing token used to pair with the electronic device. It will be appreciated that the type of pairing token presented at the display may depend on the type of display. For example, the display of a wrist-worn device may be sized to include 150×50 pixel members (e.g., LED lights 410 of FIG. 4), and the type of pairing token selectively employed by the wrist-worn device may be suitable for the type of display. It will be appreciated that the electronic device may include other types of displays, e.g., a liquid crystal display (LCD), light-emitting diode display (LED), plasma display, electronic paper display, and other types of displays suitable for presenting an optical pairing token to a computing device. The electronic device may therefore selectively employ pairing tokens suitable for presentation at these other types of displays as well.

Aspects of the disclosure have been described in terms of illustrative embodiments thereof. Numerous other embodiments, modifications and variations within the scope and spirit of the appended claims will be apparent from a review of this disclosure. For example, the steps illustrated in the illustrative figures may be performed in other than the recited order, and one or more steps illustrated may be optional in accordance with aspects of the disclosure.

What is claimed is:

1. A non-transitory computer-readable medium having executable instructions stored thereon for initializing an electronic device, wherein the instructions, when executed by a processor of a computing device, cause the computing device to:
   read, using an optical input device of the computing device, an electronic display of the electronic device to obtain input corresponding to a pairing token presented at the display;
   process the input to identify the pairing token;
   provide the pairing token to the electronic device during a handshake process that establishes a wireless communication session between the computing device and the electronic device; and
   perform an initialization process via the wireless communication session, wherein the initialization process initializes the electronic device such that the electronic device is available for operation by a user of the electronic device following the initialization process,
   wherein the initialization process comprises providing, to the electronic device, configuration information that governs operation of the electronic device and the configuration information comprises at least one user-specified configuration setting that customizes operation of the electronic device for the user.

2. The non-transitory computer-readable medium of claim 1, wherein:
   the initialization process further comprises providing, to the electronic device, at least one of a software update or a firmware update.

3. The non-transitory computer-readable medium of claim 2, wherein:
   at least one of the software update or the firmware update is issued after shipping the electronic device to a retailer and before purchase of the electronic device by the user.

4. The non-transitory computer-readable medium of claim 1, wherein:
the initialization process further comprises providing, to the electronic device, user profile information associated with the user.

5. The non-transitory computer-readable medium of claim 4, wherein:
the user profile information comprises at least one of a height of the user, a weight of the user, or a gender of the user.

6. The non-transitory computer-readable medium of claim 1, wherein:
the initialization process is performed prior to at least one of a first use of the electronic device by the user or a creation of a user profile for the user.

7. The non-transitory computer-readable medium of claim 1, wherein:
processing the input to identify the pairing token comprises at least one of:
performance of an optical character recognition process to recognize one or more alphabetic, numeric, or alphanumeric characters presented at the electronic display of the electronic device,
performance of a barcode reading process to read a barcode presented at the electronic display of the electronic device,
performance of a pattern recognition process to recognize a pattern presented at the electronic display of the electronic device,
performance of an image recognition process to recognize an image presented at the electronic display of the electronic device, or
performance of a color recognition process to recognize a color presented at the electronic display of the electronic device.

8. A non-transitory computer-readable medium comprising executable instructions stored thereon that, when executed by a processor of an electronic device, cause the electronic device at least to:
generate a pairing token locally at the electronic device;
present the pairing token at an electronic display of the electronic device for optical reading by a computing device;
establish a wireless communication session with the computing device through a pairing process that uses the pairing token optically read by the computing device from the electronic display; and
perform an initialization process upon establishing the wireless communication session such that the electronic device is available for operation by a user of the electronic device following the initialization process,
wherein the initialization process comprises receiving, from the computing device, configuration information that governs operation of the electronic device and the configuration information comprises at least one user-specified configuration setting that customizes operation of the electronic device for the user.

9. The non-transitory computer-readable medium of claim 8, wherein:
the initialization process further comprises receiving, from the computing device, at least one of a software update or a firmware update.

10. The non-transitory computer-readable medium of claim 8, wherein:
the initialization process further comprises receiving, from the computing device, user profile information associated with the user.

11. The non-transitory computer-readable medium of claim 10, wherein:
the user profile information comprises at least one of a height of the user, a weight of the user, or a gender of the user; and
the instructions, when executed by the processor of the electronic device, further cause the electronic device to generate energy expenditure information based on the user profile information.

12. The non-transitory computer-readable medium of claim 8, wherein:
the initialization process is performed prior to at least one of a first use of the electronic device by the user or a creation of a user profile for the user.

13. The non-transitory computer-readable medium of claim 8, wherein the non-transitory computer-readable medium further comprises instructions that, when executed by the processor, further cause the electronic device at least to:
generate the pairing token in response to an initial activation of the electronic device by the user.

14. The non-transitory computer-readable medium of claim 8, wherein:
the electronic device is one of:
an activity monitoring device that obtains movement information characterizing movement of the user, wherein the activity monitor obtains the movement information regardless of the user's proximity to or interaction with another computing device,
a fitness monitoring device that obtains athletic information characterizing movement of the user during performance of an athletic activity, or
a sporting device that obtains sporting information associated with the user's performance of a sporting activity.

15. The non-transitory computer-readable medium of claim 8, wherein:
the electronic device comprises one or more athletic data acquisition units, each athletic data acquisition unit being configured to measure an athletic parameter associated with the user.

16. The non-transitory computer-readable medium of claim 8, wherein:
the electronic device is configured to be worn by the user around a wrist of the user, an arm of the user, an ankle of the user, or a neck of the user;
the electronic device is configured to be attached to an article of clothing worn by the user; or
the electronic device is formed within an article of clothing worn by the user.

* * * * *